United States Patent [19]

Isoda et al.

[11] Patent Number: 5,260,280
[45] Date of Patent: Nov. 9, 1993

[54] BACTERIAL TOXIN NEUTRALIZER

[75] Inventors: Hiroko Isoda, Sapporo; Yoshihiro Kawasaki, Kawagoe; Morimasa Tanimoto, Sayama; Shunichi Dosako, Urawa; Tadashi Idota, Kawagoe, all of Japan

[73] Assignee: Snow Brand Milk Products Co., Ltd., Sapporo, Japan

[21] Appl. No.: 913,491

[22] Filed: Jul. 14, 1992

Related U.S. Application Data

[62] Division of Ser. No. 7,473,761, Feb. 2, 1990, abandoned.

[30] Foreign Application Priority Data

Feb. 7, 1989 [JP] Japan .................................. 1-027823

[51] Int. Cl.$^5$ ............................................ A61K 31/715
[52] U.S. Cl. .......................................... 514/25; 514/54; 536/17.2; 424/406
[58] Field of Search ............... 514/25, 54; 536/17.2; 424/499, 406

[56] References Cited

U.S. PATENT DOCUMENTS

| | | | |
|---|---|---|---|
| 4,347,244 | 8/1982 | Mynard et al. | 424/180 |
| 4,415,733 | 11/1983 | Tayot | 536/53 |
| 4,665,060 | 5/1987 | Mardh et al. | 514/54 |
| 4,762,822 | 8/1988 | Ettinger et al. | 514/25 |
| 5,089,479 | 2/1992 | Krivan et al. | 514/25 |

FOREIGN PATENT DOCUMENTS

| | | |
|---|---|---|
| 0036372 | 9/1981 | European Pat. Off. . |
| 0016702 | 10/1981 | European Pat. Off. . |

OTHER PUBLICATIONS

Zschocke et al., Arnzeim.-Forsch. 24, (5) 726.736, 1987.
Gyr, K., Acta Histochemica, Suppl. 29, 95–102 (1984).
Patents Abstracts of Japan 9, No. 205, (C–299) (1928) Aug. 22, 1987.
Patent Abstracts of Japan 10, No. 156 (C–351) (2212) Jun. 5, 1986.
Patent Abstracts of Japan 13, No. 107 (C–576) (3455) Aug. 22, 1987.

*Primary Examiner*—Michael G. Wityshyn
*Assistant Examiner*—C. Sayala
*Attorney, Agent, or Firm*—Millen, White, Zelano & Branigan

[57] ABSTRACT

Sialic acid binding proteins, sialic acid-binding peptides and sialic acid containing oligo-saccharides are active ingredients of a novel bacterial enterotoxin neutralizer and interfere with the binding of enterotoxins, including cholera toxin, to receptors so as to exert an effect of neutralizing the toxicity, thus being utilized as an effective neutralizer and are safe and available cheaply and abundantly from by-products produced during the processing of cow's milk which renders the enterotoxin neutralizer economically advantageous for commercial use.

11 Claims, 8 Drawing Sheets

BACTERIAL TOXIN NEUTRALIZER

This is a division, of application Ser. No. 07/473,761 filed Feb. 2, 1990, now abandoned.

BACKGROUND OF THE INVENTION

1) Field of the Invention

The present invention relates to a neutralizer which is effective for neutralization of bacterial enterotoxins produced by bacteria such as *Vibrio cholerae*, pathogenic *Escherichia coli* and *Salmonella*.

2) Description of the Related Art

Food poisoning due to *Vibrio cholerae* causes severe diarrhea accompanied by abdominal pain. Consequently, patients infected with *Vibrio cholerae* are suffered from extreme dehydration due to the diarrhea and, in the worst case, die due to the dehydration. It is well known that the severe diarrhea observed in the case of food poisoning due to *vibrio cholerae* is caused by an enterotoxin called cholera toxin which *Vibrio cholerae* produces extracellularly. The cholera toxin is a protein with a molecular weight of 84,000 consisting of one A-subunit and five B-subunits. It is said that, among them, B-subunits bind to receptors located on a mucous cell of the small intestine, while the A component invades into the cell and increases the amount of cyclic-AMP within the cell, causing change in membrane permeability, which induces exudation of intracellular fluid and salts outside the cell and thus causes diarrhea. This kind of toxins are isolated also from pathogenic *E. coli* and *Salmonella*, and are believed to be largely responsible for causing food poisoning.

The receptors which are present on the mucous cells of the small intestine has been confirmed to be liposaccharides; gangliosides such as $G_{M1}$ are identified as receptors for the cholera toxin. The utilization of this $G_{M1}$ as a cholera toxin neutralizer has already been attempted. For example, Japanese Patent Publication No. 500138/1981 disclosed a technique in which gangliosides such as $G_{M1}$ possessing a potent ability of neutralizing the cholera toxin were immobilized on latex or the like and used as neutralizing agents. Furthermore, Japanese Patent Laid-Open No. 72819/1980 disclosed a technique in which fat globule membranes in cow's milk were treated by heat and used as a toxin neutralizer without extracting gangliosides, $G_{D3}$, $G_{M2}$ and $G_{M3}$, contained in the fat globular membranes.

However, at the present time $G_{M1}$ is known to be available only in a minute amount, for example, in the bovine brain. Therefore, it was difficult to supply such $G_{M1}$ at a low cost in a large amount. Furthermore, the methods of using milk fat globular membranes in cow's milk or the like have disadvantages such that concentrations of the resulting gangliosides, which are effective components in the milk globular membranes are not consistent, and their compositions are not stable.

SUMMARY OF THE INVENTION

The present invention is a result of the intensive investigations on enterotoxins such as the cholera toxin, and thus an object of the present invention is to provide a bacterial enterotoxin neutralizer which has a potential ability to neutralize bacterial toxins produced by *Vibrio cholerae*, pathogenic *E. coli* and *Salmonella* and which is safe and can be supplied at a low cost and in abundance.

Further, the enterotoxins as used herein include cholera toxin and enterotoxins derived from pathogenic *E. coli*.

According to the present invention, sialic acid-binding proteins, sialic acid-binding peptides, and sialic acid-containing oligosaccharides, which are effective components of the neutralizer of the present invention, all interfere with the binding of bacterial enterotoxins including the cholera toxin to receptors and thus exert a toxin neutralizing effect; hence the present invention can be effectively applicable to provide a neutralizer for the above-mentioned bacterial enterotoxins. Furthermore, the above-mentioned components of the neutralizer according to the present invention are confirmed to be safe and obtainable at a low cost and in abundance from waste products produced in processes of cow's milk or the like, hence being practical from a viewpoint of cost price.

According to the present invention, a non-toxic neutralizer for bacteria enterotoxins such as the cholera toxin can be supplied consistently and at a low cost.

DETAILED DESCRIPTION OF THE INVENTION

Figure 1:
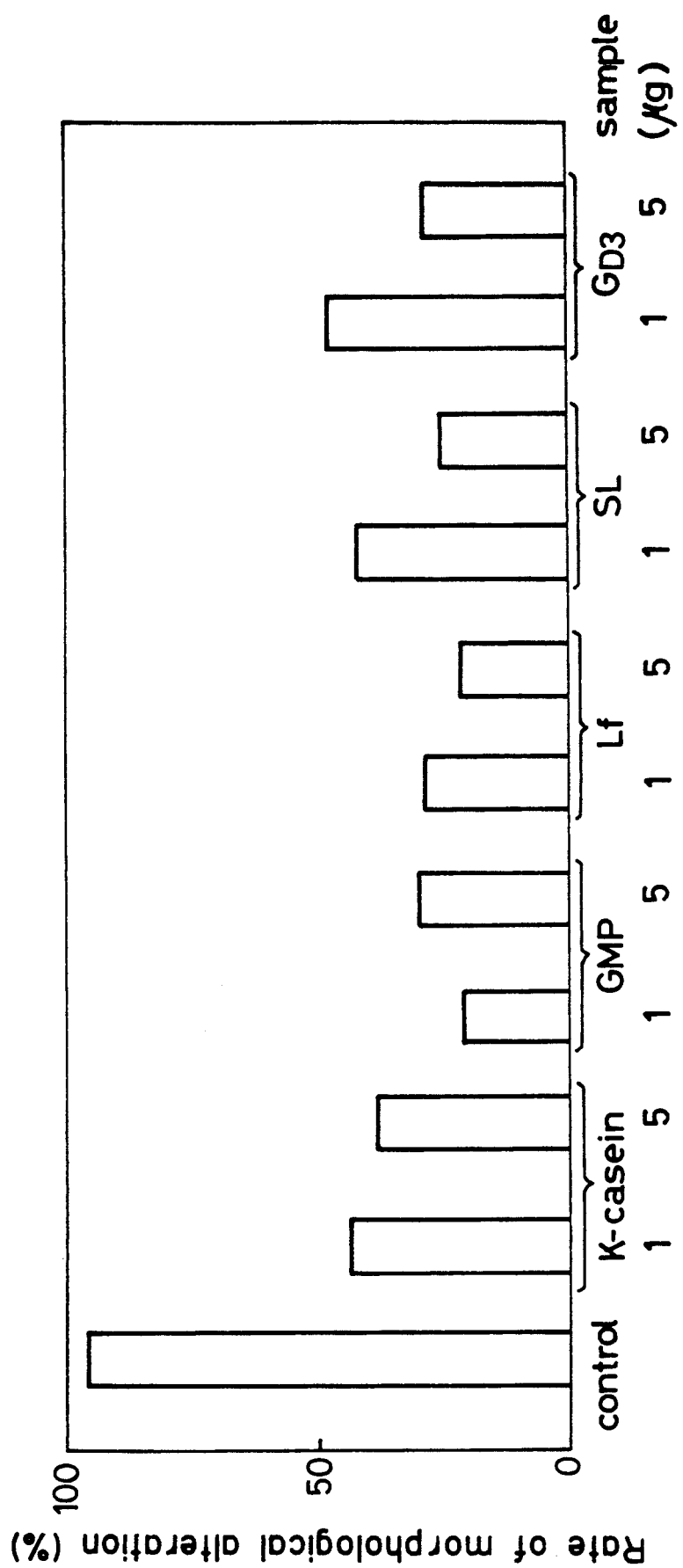
FIGS. 1 to 3 demonstrate the interfering effect of individual effective components of the bacterial toxin neutralizer according to the present invention on morphological alteration of CHO-K1 cell caused by different toxins.

The present invention is characterized in that any one or more of sialic acid-binding proteins derived from milk, sialic acid-binding peptides which can be obtained by treating sialic acid-binding proteins with protease or sialic acid-containing oligosaccharides are useful as a bacterial enterotoxin neutralizer.

Sialic acid-binding proteins derived from cow's milk used in the present invention are glycoproteins present in cow's milk and are exemplified by kappa-casein and lactoferrin. Kappa-casein is generally present in cow's milk as a constituent of casein micelles, accounts for about 11% of the total casein in cow's milk. It can be obtained from a casein fraction by known methods such as the isoelectric precipitation method. Furthermore, the ultrafiltration method disclosed in Japanese Patent Laid open No. 918/1984 can also be used.

Lactoferrin is an iron-binding protein contained in a milk whey fraction of cow's milk and can be obtained by the known gel filtration method or the like. Furthermore, the method disclosed in Japanese Patent Laid-Open No. 145200/1986 in which anti-lactoferrin antibody is used can also be employed.

Sialic acid-binding glycoproteins such as kappa-casein or lactoferrin thus obtained can be used as a bacterial enterotoxin neutralizer. Sialic acid-binding peptides which are produced by treating these sialic acid-binding proteins with protease can similarly be used. In particular, kappa-casein glycomacropeptides (hereinafter referred to as GMP) which can be obtained by treating kappa-casein with rennet are recovered from rennet-treated casein whey. Furthermore, sialic acid-binding peptides other than GMP can be obtained by reacting sialic acid-binding proteins obtained from cow's milk with protease and then fractionating using known isolation processes, such as gel filtration, ion-exchange chromatography and affinity chromatography, singly or in combination.

Further, any enzymes which belong to endopeptidase can be used as the above-mentioned protease; for example, pepsin, trypsin, papain, chymotrypsine, pronase, rennet, pancreatin or physin can be used. An example of the methods of obtaining sialic acid-binding peptides is the one disclosed in Japanese Patent Laid-Open No. 284133/1988, and an example of the methods of obtaining GMP is the one disclosed in Japanese Patent Laid-Open No. 284199/1988.

Any oligosaccharide having sialic acid at the end of the sugar chains can be used as sialic acid-binding oligosaccharides. Furthermore, any synthesized chemicals or any components extracted from natural products can also be used. For example, sialyllactose obtained in the manner disclosed in Japanese Patent Laid-Open 181497/1984, sialic acid derivatives disclosed in Japanese Patent Laid-Open 12695/1986 or further saccharide chains which are specific to gangliosides, such as $G_{D3}$, $G_{M1}$ and $G_{M3}$, can also be used for this purpose.

Among these sialic acid-containing oligo-saccharides, the above-mentioned sialyllactose which is contained in abundance in cow's milk is particularly preferable from a viewpoint of the object of the present invention.

The sialic acid-binding proteins, sialic acid-binding peptides and sialic acid-binding oligosaccharides, as mentioned above, can be used independently or as a mixture. An enterotoxin neutralizer can be optionally prepared by using known excipients or diluting agents. Amounts of the standard doses of the above-mentioned sialic acid-containing substances vary depending on the kind of toxins involved. It may, however, be mentioned that an appropriate dose of the neutralizer is in a range between 6 mg and 300 mg per day for an adult. Furthermore, if desired, it can be mixed in food or administered to animals such as live stock by mixing in feeds for the prevention of diseases.

The sialic acid-binding proteins and sialic acid-binding peptides according to the present invention are proteins derived from cow's milk and enzyme hydrolytic products of these proteins, respectively, and hence they are absolutely safe. Furthermore, their supply is sufficiently securable as milk proteins. In particular, since GMP can be recovered from cheese whey which is conventionally abundant as a by-product produced during a cheese manufacturing process, it can be supplied at further low cost.

Sialic acid-containing oligosaccharides are also distributed widely in nature and their safety is confirmed. Sialyllactose can be recovered from cheese whey according to the method disclosed in Japanese Patent Laid-Open No. 184197/1984.

Figure 2:
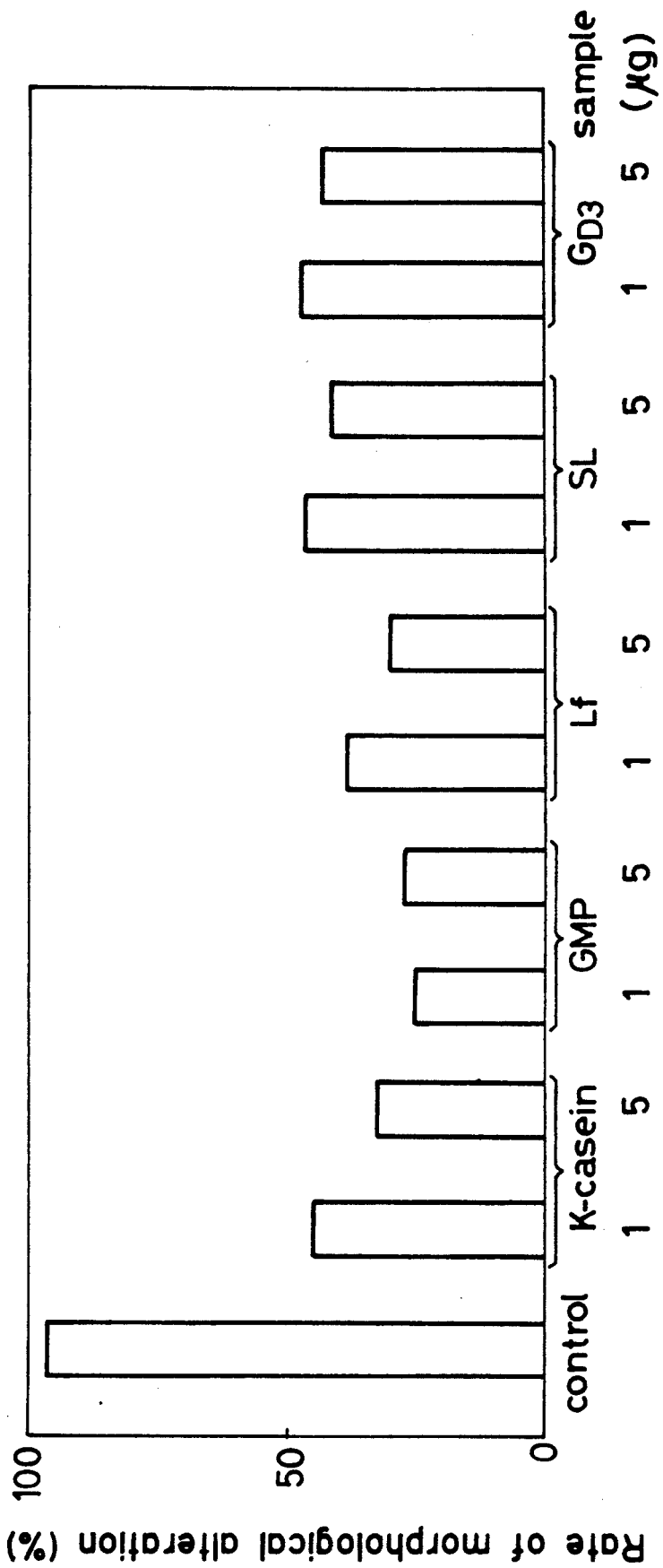
Figure 3:
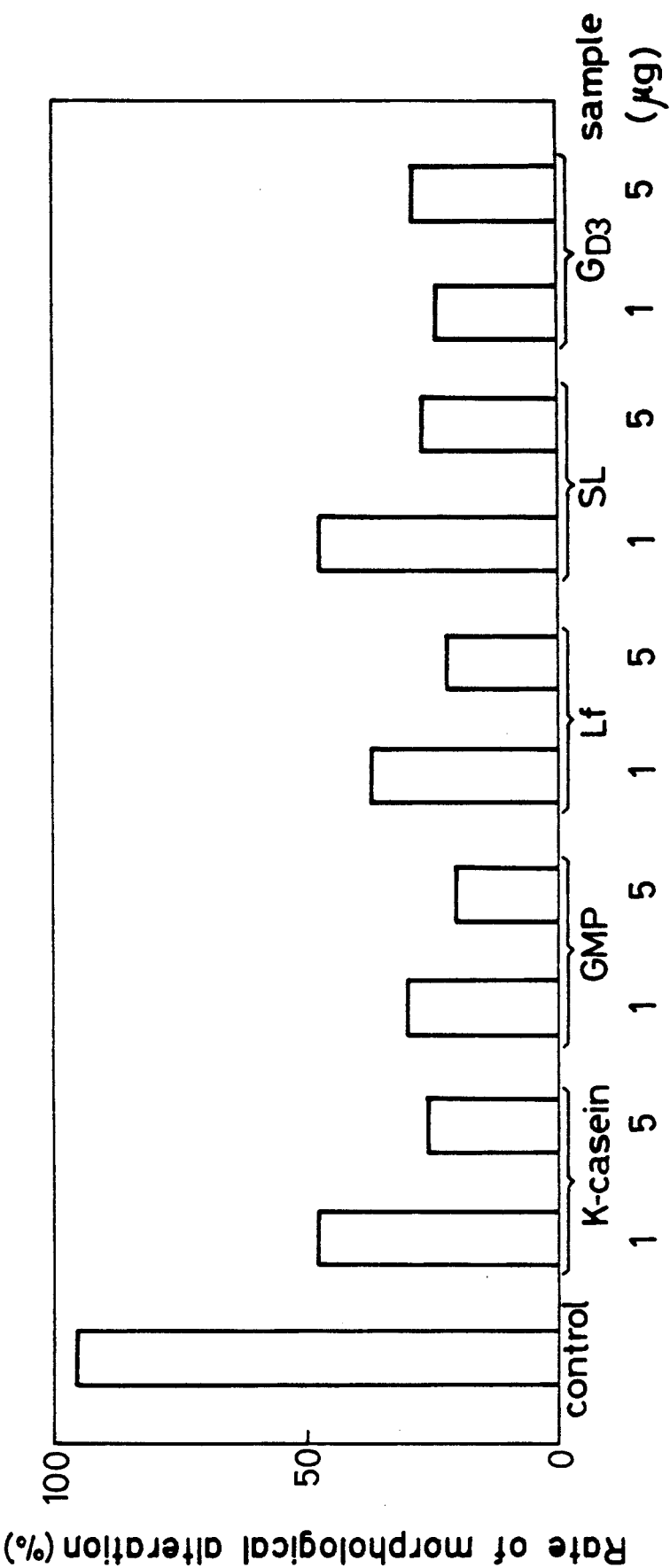
Figure 4:
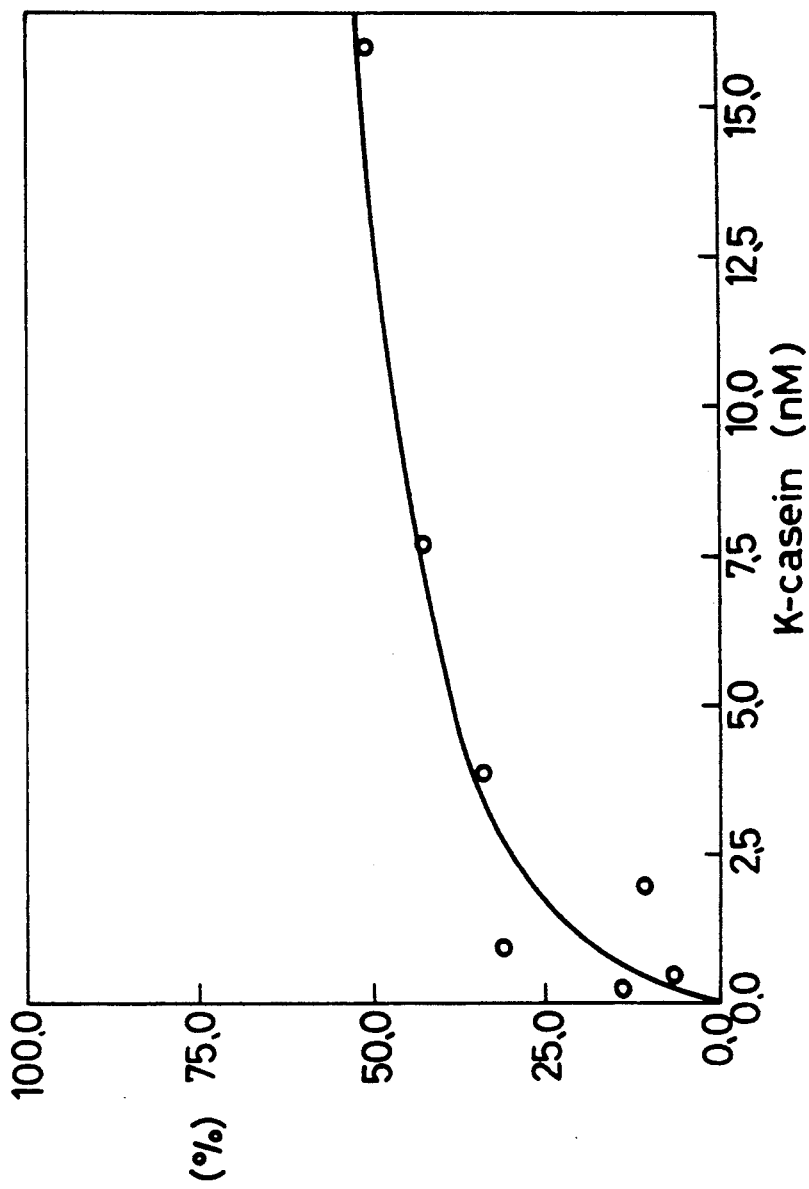
FIGS. 4 to 8 demonstrate the interfering effect of the neutralizer according to the present invention on the binding of the cholera toxin to ganglioside $G_{M1}$.
Figure 5:
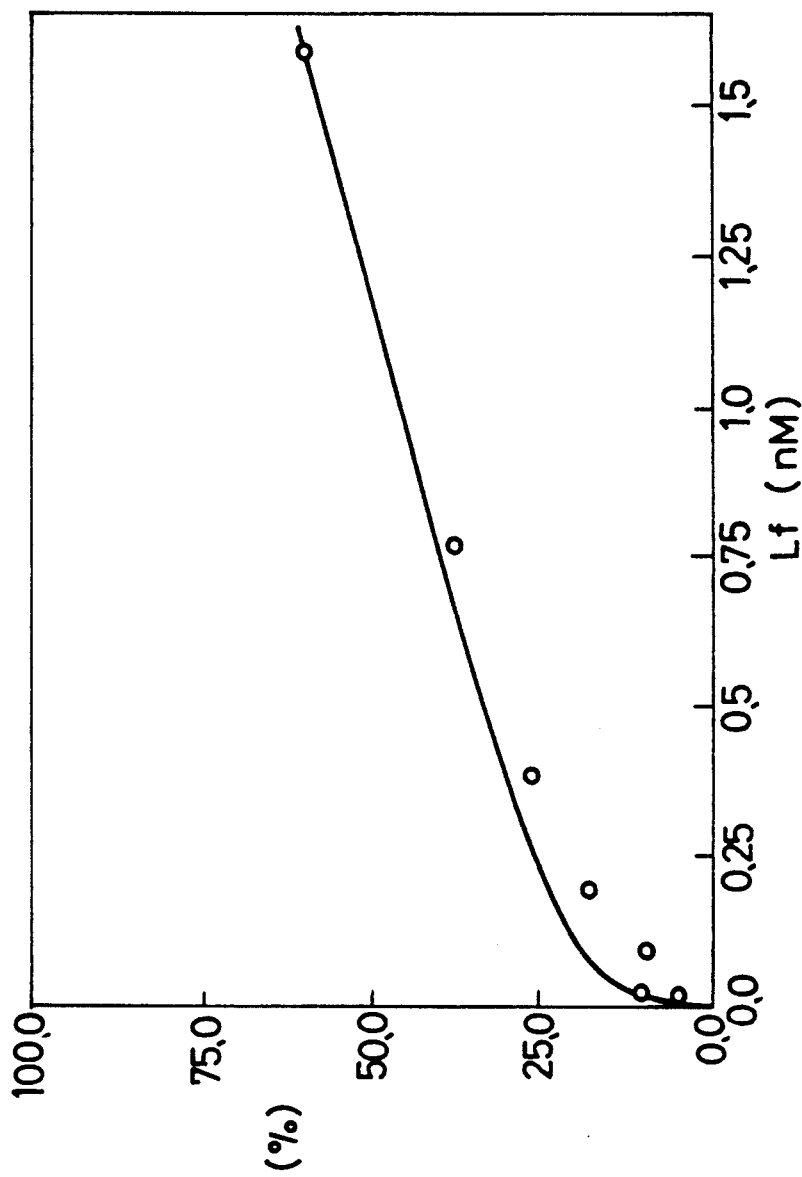
Figure 6:
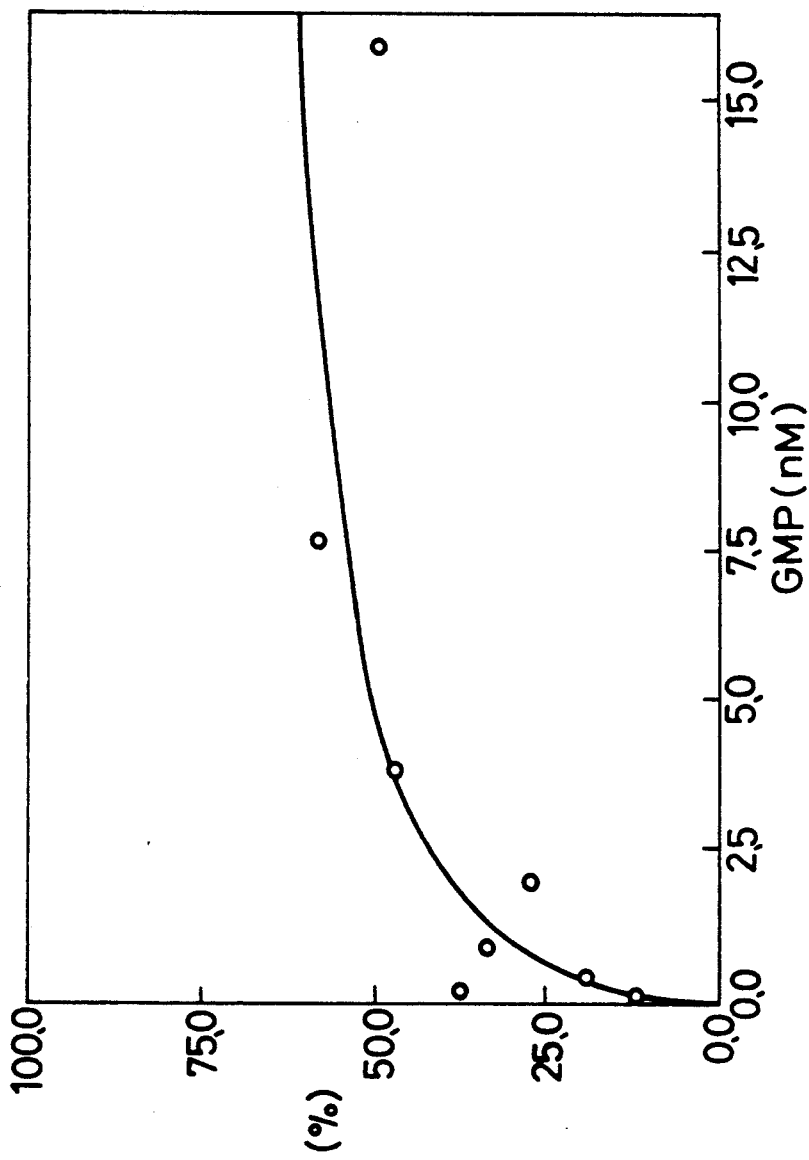
Figure 7:
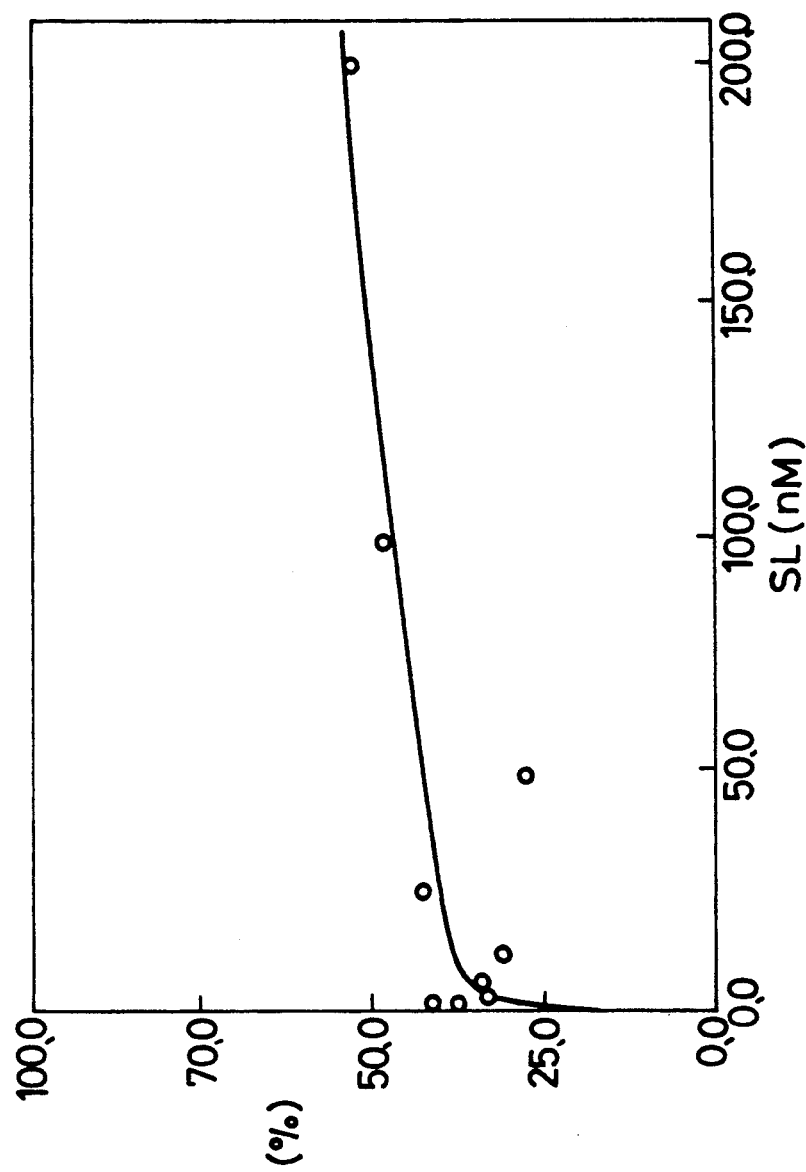
Figure 8:
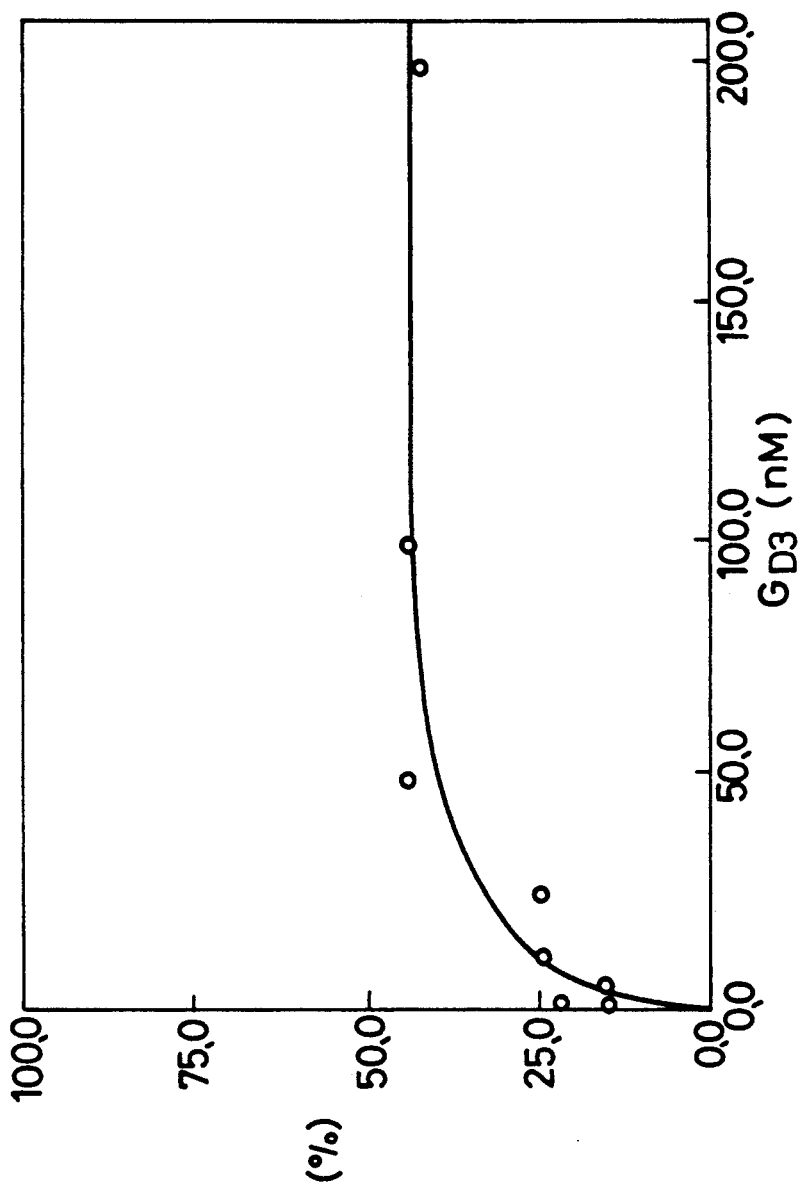

In composition aspects, this invention relates to a composition useful as bacterial enterotoxin neutralizer, which contains as an effective component one of more kinds of sialic acid-containing substances selected from the group consisting of proteins with bound sialic acid derived from cow's milk, proteins with bound sialic acid proteins with sialic protease and oligosaccharides with bound sialic acid, for example, in which the protein, peptide, or oligosaccharides with bound sialic acid is lactoferrin or kappa-casein, kappa-casein glycomacropeptide or sialyllactose. The composition can, for example, be in the form of a tablet containing 100 mg of lactoferrin per tablet, a powdered preparation for injection, containing said kappa-casein glycomacropeptide and adapted at a rate of 10% (w/v), or a granular composition prepared by mixing ganglioside $G_{D3}$, lactoferrin, kappa-casein glycomacropeptide and sialyllactose, at rates of 10%, 50%, 30% and 10%, respectively, and granulating the resultant mixture.

The following examples will demonstrate the enterotoxin neutralizing activity of the enterotoxin neutralizer of the present invention.

EXPERIMENTAL EXAMPLE 1

Test for inhibitory effect on morphological alteration of Chinese hamster ovary cells due to the cholera toxin and pathogenic *E. coli* enterotoxins (1) Determination of concentrations of the cholera toxin and enterotoxin used for measurement of activity for morphologically altering Chinese hamster ovary cells Two kinds of toxin producing *E. coli* strains (from Tokyo Municipal Institute; serotype H-10407-P strain and Pb-176 strain) which produce two kinds of antigenically different enterotoxins, enterotoxin CFA/I(LT-1) and enterotoxin CFA/II(LT-II), were cultivated with shaking in an ordinary CAYE medium. The culture was centrifuged, and the resultant supernatant was diluted stepwise from 1/10 to 1/1000 and then each diluted fluid was dispensed in a Lab-Tek 8 chamber plate (Flora Laboratories) placed on ice. The cholera toxin CT (List Biological Laboratories) was diluted in the same manner and then placed in a Lab-Tek 8-chamber plate (hereinafter referred to simply as 8-chamber plate). Subsequently, 400 microliters each of Dulbecco's medium containing 1% fetal calf serum (FCS/DMEM) was dispensed in chambers of the 8-chamber plate, then 50 microliters of a cell suspension in which Chinese hamster ovary Kl cells (CHO-Kl cell (ATCC CCL6)) cultured in 10% FCS/DMEM were suspended in 10% FCS/DMEM at a concentration of 5000 cells/ml was dispensed in the chambers, and the chamber plate was incubated at 37° C. overnight in an incubator with $CO_2$ at a concentration of 5%. Thereafter, the medium was discarded and the inside of the chambers were washed with phosphate-buffered saline (PBS(−)). Then the cells inside the chambers were soaked in methanol for 10 minutes, fixed, stained with a Giemsa stain solution and-then dried in air.

Cells amounting 200 to 400 per sample were observed under microscope and the ratios of morphologically altered cell numbers were counted so as to calculate the morphological alteration rates of CHO-Kl cells at individual concentrations of each toxin.

It was revealed that at least 70% of CHO-Kl cells were morphologically altered by CT at a concentration of 10 micrograms/ml and by undiluted supernatants of LT-I and LT-II. In Experimental Examples hereinafter, individual toxins were used at these concentrations.

(2) Activity of interfering with CHO-Kl cell morphological alteration

Activity of interfering with morphological alteration of cell caused by enterotoxins was confirmed using kappa-casein and lactoferrin (Lf) as sialic acid-binding proteins, GMP as a sialic acid-binding peptide and sialyllactose (SL) as a sialic acid-containing oligosaccharide. Furthermore, the activity was confirmed also with ganglioside $G_{D3}$. In each chamber of the 8-chamber plate placed on ice, 10 microliters of 10 micrograms/ml of CT or the culture supernatants of LT-I or LT was dispensed and then 50 microliters of individual samples at a desired concentration in a PBS(−) solution was added, and then the plate was shaken for reaction. Subsequently, 400 microliters of 1% FCS/DMEM and 50 microliters of CHO-K1 cell suspension were added to each chamber, and the plate was incubated overnight with shaking in a 5% $CO_2$ incubator. Thereafter, the methanol fixation and Giemsa staining were carried out, and then the rates of morphologically altered cells were determined. The rates of morphological alteration by individual toxins, CT, LT-I and LT-II, with the addition of the samples at the amount of 1 micrograms/chamber or 5 micrograms/chamber are shown in FIGS. 1, 2 and 3.

It was confirmed that kappa-casein, Lf, GMP and SL all neutralized the toxicity of CT, LT-I and LT-II against CHO-K1 cells.

(3) Inhibitory effect on the binding of CT to ganglioside $G_{M1}$

As described above, CT exerts the toxicity when the B-subunits bind to ganglioside $G_{M1}$ receptor on the surface of a cell and then A subunit invades into the cell. The activity of interfering with the binding of $G_{M1}$ to the cholera toxin B subunits was examined.

In each well of a 96-flat-bottom well plate, 50 microliters of a $G_{M1}$ ethanol solution (1 microgram/ml) was dispensed and then ethanol was dried by evaporation so that $G_{M1}$ was adsorbed on the plate. Each well thus treated was filled with a 1% bovine serum albumin PBS solution (BSA/PBS), allowed to stand for 1 hour and then washed three times with PBS containing 0.05% Tween 20 (PBS Tween 20). On the other hand, each sample was made up to a 1% BSA/PBS solution, 25 microliters of each sample was previously mixed with 25 microliters of a 1% solution of peroxidase-labeled cholera toxin B-subunits (PO-CT-B) in BSA/PBS (1 microgram/ml), and the mixture was incubated at room temperature for 30 minutes. These mixtures were added to the wells of the above-mentioned $G_{M1}$-adsorbing plate. After standing for 30 minutes, each well was washed six times with PBS Tween 20 and added with 100 microliters of 0.2 M citric acid buffer (pH 4.0) containing 2,2'-azinobis(3-ethylbenzthiazoline sulfonic acid-2-ammonium (ABTS) at a concentration of 0.3 mg/ml dissolved in 0.006% $H_2O_2$. After 10 minutes, the rates of binding of $G_{M1}$ to the cholera toxin B-subunits were estimated by measuring the absorbance at 405 nm.

As demonstrated in FIGS. 4 to 8, all the samples interfered with the binding of the cholera toxin B-subunits to $G_{M1}$ depending on the concentration.

From the results described above, it was confirmed that kappa-casein, Lf, GMP and SL neutralized the toxicity of bacterial enterotoxins and interfered with the binding of the enterotoxins to the cell receptors.

The following Examples explain the present invention in more detail.

EXAMPLE 1

Effect of neutralizing the toxicity of cholera toxin

Eighty Balb/c young mice, weighing about 20 grams, were divided into 16 groups, 5 mice in each group. One group was used as a control and the remaining 15 groups were further divided into 5 groups; the animals in each group were administered with samples, i.e. kappa-casein, Lf, GMP, SL and $G_{D3}$. The administration was carried out orally for 7 days at doses of 0.2, 0.5 and 1.0 mg/day/mouse. On day 8, a mixture of 0.25 mg of CT with water or each sample was orally administered, and thereafter, incidence of diarrhea in the mice was observed.

As shown in Table 1, the group administered with the samples all demonstrated drastic decreases in the rate of the incidence of diarrhea as compared with the control group.

TABLE 1

| Sample | In vivo activity of neutralizing the toxicity of cholera toxin | |
|---|---|---|
| | Dose (mg/day) | Rate of diarrhea (%) |
| Control | — | 100 |
| Kappa-casein | 0.2 | 60 |
| | 0.5 | 20 |
| | 1.0 | 20 |
| GMP | 0.2 | 60 |
| | 0.5 | 20 |
| | 1.0 | 0 |
| Lf | 0.2 | 60 |
| | 0.5 | 40 |
| | 1.0 | 20 |
| SL | 0.2 | 20 |
| | 0.5 | 20 |
| | 1.0 | 0 |
| $G_{D3}$ | 0.2 | 20 |
| | 0.5 | 20 |
| | 1.0 | 0 |

EXAMPLE 2

Effect of neutralizing the toxicity of enterotoxin Lt-1 derived from pathogenic E. coli Effects of neutralizing the toxicity of LT-I of individual samples were confirmed by the same test method as described in Example 1. LT-I used for administration was 100 microliters of the culture supernatant as described in Experimental Example 1.

As shown in Table 2, the group administered with individual samples all demonstrated drastic decreases in the rates of the incidence of diarrhea as compared with the control group.

TABLE 2

| Sample | In vivo activity of neutralizing the toxicity of enterotoxin LT-I | |
|---|---|---|
| | Dose (mg/day) | Rate of diarrhea (%) |
| Control | — | 100 |
| Kappa-casein | 0.2 | 80 |
| | 0.5 | 40 |
| | 1.0 | 20 |
| GMP | 0.2 | 60 |
| | 0.5 | 20 |
| | 1.0 | 20 |
| Lf | 0.2 | 40 |
| | 0.5 | 40 |
| | 1.0 | 20 |
| SL | 0.2 | 40 |
| | 0.5 | 20 |
| | 1.0 | 20 |
| $G_{D3}$ | 0.2 | 60 |
| | 0.5 | 20 |
| | 1.0 | 20 |

EXAMPLE 3

Effects of neutralizing the toxicity of enterotoxin LT-II derived from pathogenic E. coli Effects of neutralizing toxicity of LT-II of individual samples were confirmed by the same test method as described in Example 1. 100 microliters of the culture supernatant of LT-II was used for administration as described in Experimental Example 1.

As shown in Table 3, the group administered with individual samples all demonstrated drastic decreases in the rate of the incidence of diarrhea as compared with the control group.

TABLE 3

| | In vivo activity of neutralizing the toxicity of enterotoxin LT-II | |
|---|---|---|
| Sample | Dose (mg/day) | Rate of diarrhea (%) |
| Control | — | 100 |
| Kappa-casein | 0.2 | 60 |
| | 0.5 | 60 |
| | 1.0 | 20 |
| GMP | 0.2 | 40 |
| | 0.5 | 20 |
| | 1.0 | 0 |
| Lf | 0.2 | 60 |
| | 0.5 | 20 |
| | 1.0 | 20 |
| SL | 0.2 | 40 |
| | 0.5 | 20 |
| | 1.0 | 0 |
| $G_{D3}$ | 0.2 | 40 |
| | 0.5 | 40 |
| | 1.0 | 20 |

Further, the following Examples illustrate the preparation of the bacterial enterotoxin neutralizer according to the present invention.

EXAMPLE 4

Ten grams of lactoferrin and 100 grams of lactose were mixed, and the mixture was prepared in a tablet form using a machine. The resultant tablets contain 100 mg lactoferrin per tablet and can be used for oral administration.

EXAMPLE 5

Ten grams of kappa-casein glycomacropeptide (GMP) was dissolved in 1 liter of saline, and the solution was heated in an autoclave at 121° C. for 10 minutes. The resultant solution, 2 ml each, was dispensed into 5 ml-volume vials; immediately after lyophilization, the vials were sealed to prepare a powdered pharmaceutical preparation for injection.

The obtained pharmaceutical preparation is used by dissolving with an addition of 2 ml of distilled water.

EXAMPLE 6

Ten grams of $G_{D3}$, 50 grams of lactoferrin, 30 grams of GMP and 10 grams of sialyllactose (SL) were mixed, degraded and then granulated. The resultant granular mixture, 100 mg each, was filled in gelatin capsules to prepare 1000 pharmaceutical capsules.

We claim:

1. A method of neutralizing bacterial enterotoxins which comprises administering to a human being suffering from the effects of the enterotoxin an amount of isolated sialyllactose effective to ameliorate those effects.

2. A method as set forth in claim 1, wherein the sialyllactose is administered in tablet, granular or powder form.

3. A method as set forth in claim 2, wherein the sialyllactose is administered in tablet form.

4. A method as set forth in claim 2, wherein the sialyllactose is administered in granular form.

5. A method as set forth in claim 2, wherein the sialyllactose is administered orally.

6. A bacterial enterotoxin neutralizer composition in solid unit dosage form which comprises, per unit dosage, a bacterial enterotoxin neutralizing amount, in admixture with a pharmaceutically acceptable carrier, of at least one isolated sialic acid-containing substance comprising sialyllactose.

7. A bacterial enterotoxin neutralizer composition as set forth in claim 6, in tablet, granule or powder form.

8. A bacterial enterotoxin neutralizer composition as set forth in claim 6, as a powdered preparation adapted for injection, as an aqueous solution thereof.

9. A bacterial enterotoxin neutralizer composition as set forth in claim 6, in granular form.

10. A bacterial enterotoxin neutralizer composition as set forth in claim 6 in tablet form.

11. A capsule containing a composition of claim 6, in granular form.

* * * * *

UNITED STATES PATENT AND TRADEMARK OFFICE
CERTIFICATE OF CORRECTION

PATENT NO. : 5,260,280

DATED : November 9, 1993

INVENTOR(S) : Hiroko ISODA et al.

It is certified that error appears in the above-identified patent and that said Letters Patent is hereby corrected as shown below:

TITLE PAGE; ITEM 62; Related U.S. Application Data:

Change 7,473,761 to read -- 07/473,761 --

Signed and Sealed this

Third Day of May, 1994

Attest:

BRUCE LEHMAN

*Attesting Officer*      *Commissioner of Patents and Trademarks*